(12) United States Patent
Shenai-Khatkhate et al.

(10) Patent No.: US 7,321,048 B2
(45) Date of Patent: Jan. 22, 2008

(54) ORGANOMETALLIC COMPOUND PURIFICATION

(75) Inventors: Deodatta Vinayak Shenai-Khatkhate, Danvers, MA (US); Ronald L. DiCarlo, Jr., Danville, NH (US)

(73) Assignee: Rohm and Haas Electronic Materials LLC, Marlborough, MA (US)

( * ) Notice: Subject to any disclaimer, the term of this patent is extended or adjusted under 35 U.S.C. 154(b) by 0 days.

(21) Appl. No.: 11/600,998

(22) Filed: Nov. 17, 2006

(65) Prior Publication Data

US 2007/0117994 A1    May 24, 2007

Related U.S. Application Data

(60) Provisional application No. 60/738,117, filed on Nov. 18, 2005.

(51) Int. Cl.
　　C07F 5/06　　(2006.01)
　　C07C 395/00　(2006.01)
　　C07C 5/02　　(2006.01)

(52) U.S. Cl. ............................. 556/27; 556/1; 556/70; 556/87; 556/121; 556/187; 568/1; 568/7; 562/899; 210/634; 210/639

(58) Field of Classification Search .................. 556/1, 556/27, 70, 87, 121, 187; 568/1, 7; 562/899; 210/634, 639
See application file for complete search history.

(56) References Cited

U.S. PATENT DOCUMENTS

| 4,794,500 | A | * | 12/1988 | Bradley ..................... 362/549 |
| 4,847,399 | A | * | 7/1989 | Hallock et al. ................ 556/1 |
| 5,288,885 | A | * | 2/1994 | Smit et al. ..................... 556/1 |
| 5,350,869 | A | * | 9/1994 | Kanjolia et al. ............... 556/1 |
| 5,455,364 | A | | 10/1995 | Yako et al. .................... 556/1 |
| 5,783,717 | A | | 7/1998 | Ohsaki et al. ............... 556/187 |
| 5,951,820 | A | * | 9/1999 | Ohsaki et al. ............. 159/47.1 |
| 7,005,530 | B2 | * | 2/2006 | Nishiwaki et al. ............. 556/1 |
| 2004/0122248 | A1 | | 6/2004 | Shenai-Khatkhate et al. .. 556/7 |

* cited by examiner

*Primary Examiner*—Porfirio Nazario-Gonzalez
(74) *Attorney, Agent, or Firm*—S. Matthew Cairns

(57) ABSTRACT

A method of purifying an organometallic compound by heating the organometallic compound in the presence of a trialkyl aluminum compound and a catalyst.

10 Claims, No Drawings

ORGANOMETALLIC COMPOUND PURIFICATION

The present invention relates to the field of organometallic compounds. In particular, the present invention relates to the field of purification of organometallic compounds, particularly those used in the vapor deposition of metal-containing films.

Metal-containing compounds are used in a variety of applications, such as sources for growing thin metal films. One use of such compounds is in the manufacture of electronic devices such as semiconductors. Many semiconducting materials are manufactured using well-established deposition technologies that employ ultrapure metalorganic compounds, e.g. Metalorganic Vapor Phase Epitaxy ("MOVPE"), Metalorganic Molecular Beam Epitaxy ("MO-MBE"), Metalorganic Chemical Vapor Deposition ("MOCVD") and Atomic Layer Deposition ("ALD"). To be useful in these processes the organometallic compounds must be free from contaminants and/or deleterious impurities. If not removed, such impurities present in the organometallic sources can cause adverse effects on the electronic and/or optoelectronic properties of electronic devices.

Silicon and oxygen are both deleterious impurities, particularly in the growth of Group III-Group V ("III-V") and Group II-Group VI ("II-VI") compound semiconductors. Silicon can act as either an n-type or p-type dopant depending on the site it occupies in the crystal lattice of III-V compound semiconductors. The presence of trace silicon, at levels as low as one ppm, can seriously affect the total carrier concentration in the films deposited, and subsequently the performance of the devices comprised of these films. Oxygen incorporation can affect the carrier lifetime and optical efficiency of the devices produced, particularly those containing AlGaAs compounds. Silicon and oxygen are generally present in the inorganic reagents and/or the organic solvents employed in typical organometallic syntheses. These impurities, once incorporated, are extremely difficult to separate from the organometallic compounds, since their boiling points and volatilities are very close to those of target organometallic compounds.

U.S. Pat. No. 5,783,717 (Ohsaki et al.) discloses a method of removing oxygen-containing impurities from organometal compounds by mixing the organometal compound with an aluminum chloride compound of the formula $X_{6-q}Al_2R_q$, where X is chlorine, R is an alkyl having 1-3 carbons and q is an integer from 1-5. This method does not effectively remove enough of the oxygen-containing impurities to meet current industry requirements for organometallic compound purity.

The present invention solves the problems of conventional purification methods by providing organometallic compounds that have reduced levels of oxygen-containing impurities. In addition, the present invention provides organometallic compounds that have reduced levels of silicon-containing impurities as compared to those obtained using conventional purification processes. In one embodiment, the present invention provides organometallic compounds that are substantially free of oxygen-containing impurities and substantially free of silicon-containing impurities.

"Alkyl" refers to linear, branched and cyclic alkyl. Likewise, the terms "alkenyl" and "alkynyl" refer to linear, branched and cyclic alkenyl and alkynyl, respectively. The terms "a" and "an" refer to the singular and the plural. As used in this specification, the following abbreviations have the following meanings: % wt=percent by weight; g=grams; ppm=parts per million; and cm=centimeters. All percentages are by weight, unless otherwise noted. All numerical ranges are inclusive and combinable in any order, except where it is clear that such numerical ranges are constrained to add up to 100%.

As one aspect of the present invention is to provide organometallic compounds having a reduced amount of oxygen-containing impurities, all manipulations described herein are typically performed in an inert atmosphere, such as in nitrogen or argon.

The present invention provides a method of purifying an organometallic compound including i) providing a mixture including a) an organometallic compound chosen from unsymmetrical dimethyl hydrazine and a compound of the formula $R^1R^2_{n-1}M^1$ wherein $R^1$ is chosen from $(C_1-C_{20})$alkyl, $(C_2-C_{12})$dialkylamino, $(C_1-C_{12})$alkylamino$(C_1-C_{12})$alkyl, di$(C_1-C_{20})$alkylamino$(C_1-C_{12})$alkyl, $(C_2-C_{20})$alkenyl, $(C_2-C_{20})$alkynyl and aryl; each $R^2$ is independently chosen from hydrogen, $(C_1-C_{20})$alkyl, $(C_2-C_{12})$dialkylamino, $(C_1-C_{12})$alkylamino$(C_1-C_{12})$alkyl, di$(C_1-C_{20})$alkylamino$(C_1-C_{12})$alkyl, $(C_2-C_{20})$alkenyl, $(C_2-C_{20})$alkynyl, aryl and halogen; $M^1$ is a Group IIA to Group VIA metal; and n is the valence of $M^1$; and b) a purifying composition including an alkyl-metal compound of the formula $R^3_xR^4_{3-x}M^2$ wherein $R^3$ is a $(C_1-C_{20})$alkyl; each $R^4$ is independently chosen from hydrogen and halogen; $M^2$ is a Group IIIA metal; and x is an integer from 1-3; and a catalyst compound; and ii) heating the mixture. The present method is useful for reducing the level of oxygen-containing and silicon-containing impurities present in the organometallic compound.

A wide variety of organometallic compounds may be purified according to the present method. Such organometallic compounds include unsymmetrical dimethyl hydrazine and compounds of the formula (I) $R^1R^2_{n-1}M^1$ wherein $R^1$ is chosen from $(C_1-C_{20})$alkyl, $(C_2-C_{12})$dialkylamino, $(C_1-C_{12})$alkylamino$(C_1-C_{12})$alkyl, di$(C_1-C_{20})$alkylamino$(C_1-C_{12})$alkyl, $(C_2-C_{20})$alkenyl, $(C_2-C_{20})$alkynyl and aryl; each $R^2$ is independently chosen from hydrogen, $(C_1-C_{20})$alkyl, $(C_2-C_{12})$dialkylamino, $(C_1-C_{12})$alkylamino$(C_1-C_{12})$alkyl, di$(C_1-C_{20})$alkylamino$(C_1-C_{12})$alkyl, $(C_2-C_{20})$alkenyl, $(C_2-C_{20})$alkynyl, aryl and halogen; $M^1$ is a Group IIA to Group VIA metal; and n is the valence of $M^1$, although other organometallic compounds may be advantageously purified. $M^1$ may be any metal of Groups IIA, IIIA, IVA, VA and VIA. As used in this application, the term "metal" is intended to include elements of Group VA, namely phosphorus, arsenic, antimony and bismuth, which are metalloids. In one embodiment, $M^1$ is chosen from a Group IIIA, Group IVA and Group VA metal. In another embodiment, $M^1$ is chosen from aluminum, gallium, indium, boron, zinc, arsenic, antimony, bismuth and tellurium.

Exemplary organometallic compounds that may be purified according to the present method include, but are not limited to, trimethylaluminum, triethylaluminum, tri-iso-butylaluminum, tri-tert-butylaluminum, trimethylgallium, triethylgallium, trimethylindium, triethylindium, di-iso-propyl methyl indium, iso-propyl dimethyl indium, triethylboron, dimethylzinc, diethylzinc, di-isopropyl telluride, diethyltelluride, diethylselenide, di-iso-propylselenide, trimethylarsenic, trimethylantimony, triethylantimony, bis(cyclopentadienyl)magnesium, tert-butylphosphine, ethylarsine, tert-butylarsine, bisphosphinoethane, tris(dimethylamino)stibine, tris(dimethylamino)arsine, tris(dimethylamino)phosphine, tertakis(dimethylamino)silane, tertakis(dimethylamino)germane, dimethylaminopropyldimethylaluminum, isobutylgermane, triphenylphosphine, phenyl-bis-(2-dimethylaminophenyl)phosphine and phenylbis-(4-dimethylamino)phosphine. Mixtures of organometallic compounds may also be purified according to the present method.

In the present method, the organometallic compound to be purified is contacted with a purifying composition including an alkyl-metal compound and a catalyst, the alkyl-metal compound and the catalyst being different. The alkyl-metal compound and the organometallic compound are different. Similarly, the catalyst and the organometallic compound are different. The alkyl-metal compound is a compound of the formula (II) $R^3{}_xR^4{}_{3-x}M^2$ wherein $R^3$ is a $(C_1-C_{20})$alkyl; each $R^4$ is independently chosen from hydrogen and halogen; $M^2$ is a Group IIIA metal; and x is an integer from 1-3. A wide variety of alkyl-metal compounds may be suitably employed. In one embodiment, the alkyl-metal compound is a $(C_1-C_5)$alkyl-Group IIIA metal compound. In another embodiment, the alkyl-metal compound is a trialkyl-Group IIIA metal compound, typically a tri$(C_1-C_5)$alkyl-Group IIIA metal compound. Exemplary alkyl-metal compounds include, without limitation, trimethylaluminum, triethylaluminum, dimethylaluminum chloride, methyl aluminum dichloride, dimethylgallium chloride, trimethylgallium, triethylindium and trimethylindium. Mixtures of alkyl-metal compounds may also be used. In one embodiment, the alkyl group of the alkyl-metal compound is the same as the alkyl group present in the organometallic compound. In another embodiment, when $M^1$ and $M^2$ are both aluminum, it is preferred that the alkyl group on $M^2$, i.e. on the alkyl-metal compound, is a higher alkyl group than that on $M^1$, i.e. the organometallic compound. By 'higher alkyl group" is meant an alkyl group having at least one more carbon atom that the alkyl group to which it is being compared.

The catalyst may be any of a wide variety compounds, including salts, that enhance the transalkoxylation of the organometallic compound to be purified. While not wishing to be bound by theory, the inventors believe that the catalyst functions to facilitate the transfer of an alkoxy group from an oxygen-containing impurity of the organometallic compound, i.e. an oxygen-containing impurity also containing $M^1$, to the alkyl-metal compound. Suitable catalysts include, but are not limited to, compounds and salts of Group IA, IIA, and VA metals. Such catalysts typically include one or more groups chosen from hydrogen, halogen, alkyl, alkenyl, alkynyl, aryl, amino, dialkylamino, aminoalkyl, and dialkylaminoalkyl. The aryl group may be substituted, such as by replacing one or more of the hydrogens with one or more substituent groups such as halogen, cyano, amino, dialkylamino, aminoalkyl and dialkylaminoalkyl. Typically, the catalyst is free of oxygen substitution. Exemplary catalysts include, without limitation, lithium dimethylamide, tert-butyl lithium, n-butyl lithium, aluminum trichloride, aluminum tribromide, aluminum triiodide, gallium trichloride, indium trichloride, calcium dichloride, barium difluoride, tetramethyl ammonium fluoride, and tris(dimethylamino) aluminum. Mixtures of catalysts may be used.

The weight ratio of alkyl-metal compound to catalyst in the purifying composition may vary over a wide range. Typically the weight ratio of alkyl-metal compound to catalyst is from 10:1 to 1:10. More typically, the weight ratio is from 5:1 to 1:5.

The organometallic compound, alkyl-metal compound and catalyst may be combined in any order. In one embodiment, the purifying composition may be prepared first by combining the alkyl-metal compound and the catalyst and then the composition may be combined with the organometallic compound. Alternatively, the alkyl-metal compound and the catalyst may each be added to the organometallic separately, either sequentially or simultaneously. In general, the purifying composition is present in an amount of 0.1 to 10% wt based on the weight of the organometallic compound. Typically, the purifying composition is present in an amount of 0.2 to 8% wt.

After the organometallic compound is combined with the alkyl-metal compound and the catalyst, the mixture is heated. The particular heating temperature depends upon the organometallic compound, alkyl-metal compound and catalyst employed. Typically, such temperature is below that temperature at which the organometallic compound degrades. Exemplary temperatures include, but are not limited to, those in the range of 30 to 175° C. More typically, suitable temperatures are from 50 to 150° C., and still more typically from 70 to 80° C. The duration of the heating step may vary over a wide range, such as from 5 minutes to 5 hours, although shorter or longer times may be used. More typically, the heating step is from 15 minutes to 5 hours, still more typically from 30 minutes to 4 hours, and particularly from 1 to 2 hours. Such heating step facilitates the reduction in impurity levels in the organometallic compound.

Following the heating step, the purified organometallic compound is separated from the alkyl-metal compound and the catalyst. Such separation may be effected by any suitable technique, such as, but not limited to, distillation or sublimation. Other separation techniques, such as recrystallization, may be employed. These separation techniques are well known to those skilled in the art.

Organometallic compounds are obtained by the present method having reduced levels of oxygen-containing impurities and reduced levels of silicon-containing impurities. In one embodiment, the purified organometallic compounds are substantially free of oxygen-containing impurities. By 'substantially free of oxygen-containing impurities" it is meant that the purified organometallic compounds contain $\leqq 0.05$ ppm of oxygen-containing impurities. In another embodiment, the purified organometallic compounds are substantially free of silicon-containing impurities, i.e., the purified organometallic compounds contain $\leqq 0.03$ ppm of silicon-containing impurities. Typically, the purified organometallic compounds are substantially free of both oxygen-containing impurities and silicon-containing impurities. The levels of impurities can be determined by conventional Fourrier-transform nuclear magnetic resonance ("FT-NMR") spectroscopy in the case of oxygen-containing impurities and by conventional inductively coupled plasma ("ICP") analysis in the case of metallic impurities. The purified organometallic compounds obtained by the present method are typically $\geqq 99.9999\%$ pure.

The purified organometallic compounds of the present invention may be used in a variety of applications that demand the use of high purity organometallic compounds such as MOCVD applications to produce high performance devices used in voice/data communications, light emitting diodes ("LEDs"), and DVD applications. Further, many of these purified organometallic compounds may be used as alkylating reagents in the manufacture of other organometallic compounds. For example, purified trimethylaluminum may be used to manufacture trimethylindium that has substantially lower levels of silicon-containing and oxygen-containing impurities, and purified triethylaluminum may be used to manufacture triethylgallium that has substantially lower levels of silicon-containing and oxygen-containing impurities. An advantage of the present invention is that it provides a reduction in number of purification steps needed for organometallic reagents, e.g., a reduction in the number of distillations of the raw materials and/or final products.

Thus, this invention reduces cycle time significantly which leads to an overall decrease in the amount of labor involved and the overall manufacturing costs The following examples are expected to illustrate various aspects of the invention.

EXAMPLE 1

$AlCl_3$ (1 g) and triethylaluminum (3 g) were added independently to triethylboron (200 g) in a round-bottom 3-neck flask, equipped with a magnetic stirring bar. The triethylboron was known to contain 294 ppm of oxygenated impurity, based on FT-NMR analysis. The mixture was heated at 60° C. for 1 hour, and was then distilled through a 30-cm packed column and a partial take-off head at atmospheric pressure. A 40 g forerun was taken and intentionally discarded, head temperature at end of fore-run was 95.1° C. A subsequent main fraction of 130 g was then obtained, observing a constant head temperature of 95.1° C. The tail fraction was found to be approximately 30 g. Analysis of the main fraction by FT-NMR revealed oxygen impurities to be not detectable (i.e. below 0.05 ppm). Analysis of the purified triethylboron by ICP techniques revealed the absence of (i.e. not detectible) the following metallic impurities: Al, Be, Ca, Cd, Cr, Cu, Fe, Mg, Mn, Pb, Si (below 0.03 ppm), Sn, Sr, and Zn.

EXAMPLE 2

Triethylaluminum ($Et_3Al$) including oxygen-containing impurities and silicon-containing impurities is added to a distillation flask. Tri-iso-butylaluminum (2-5% wt based on the weight of $Et_3Al$) and aluminum trichloride (1% wt based on the weight of $Et_3Al$) are added to the distillation flask with continuous stirring. The mixture is heated to approximately 120° C. for 3 hours, after which the mixture is allowed to cool to room temperature. Next, vacuum is applied to perform fractional distillation at reduced pressure. A forerun of approximately 15% wt is taken and at least 15% wt is left as a tail fraction. Purified triethylaluminum that is substantially free of oxygen-containing impurities and silicon-containing impurities is expected.

EXAMPLE 3

A 5-liter stainless steel reboiler equipped with a distillation column and a reflux head is set up. To this is charged 300 g of triethylaluminum. Tri-n-propylaluminum (10 g) and indium trichloride (5 g) are then added, this corresponds to approximately 5% wt. The mixture is heated to approximately 120° C. and stirred for 3 hours, after which it is allowed to cool. Upon cooling, the system is placed under full vacuum and then heated gradually to afford a gentle reflux. The system is allowed to reflux for approximately one hour. A forerun of approximately 15% wt (~40 g) is taken. The main fraction is then collected. Approximately 15% wt of the mixture is left behind as a tail fraction. The main fraction is analyzed by ICP-optical emission spectroscopy (ICP-OES) and FT-NMR. The purified triethylaluminum is expected to be substantially free of oxygen-containing impurities and silicon-containing impurities.

EXAMPLE 4

The procedure of Example 2 is repeated except that the triethylaluminum is replaced with 250 g of diethylzinc. The amount of tri-iso-butylaluminum to be added is 10 g and the amount of aluminum trichloride to be added is 3 g. In addition, 2 g of potassium fluoride is added. Following distillation, purified diethylzinc that is substantially free of oxygen-containing impurities and silicon-containing impurities is expected to be obtained.

EXAMPLE 5

The procedure of Example 3 is repeated except that the triethylaluminum is replaced with 200 g of triethylgallium, 10 g of tri-iso-butylaluminum are used and the indium trichloride is replaced with 2 g of gallium trichloride. Purified triethylgallium that is substantially free of oxygen-containing impurities and silicon-containing impurities is expected to be obtained.

EXAMPLE 6

The procedure of Example 4 is repeated except that the diethylzinc is replaced with 220 g of unsymmetrical dimethylhydrazine. Purified unsymmetrical dimethylhydrazine that is substantially free of oxygen-containing impurities and silicon-containing impurities is expected to be obtained.

EXAMPLE 7

The procedure of Example 2 is repeated except that the triethylaluminum is replaced with 300 g of trimethylarsenic, 14 g of trimethylaluminum are used and the aluminum trichloride is replaced with 4 g of sodium fluoride and 2 g of aluminum tribromide. Purified trimethylarsenic that is substantially free of oxygen-containing impurities and silicon-containing impurities is expected to be obtained.

EXAMPLE 8

The procedure of Example 3 is repeated except that the triethylaluminum is replaced with 275 g of trimethylantimony, and 12 g of trimethylaluminum are used. Purified trimethylantimony that is substantially free of oxygen-containing impurities and silicon-containing impurities is expected to be obtained.

EXAMPLE 9

The procedure of example 4 is repeated except that the diethylzinc is replaced with 280 g of trimethylbismuth, 13 g of tri-iso-butylaluminum are added, and the aluminum trichloride is replaced with 5 g of potassium chloride and 2 g of aluminum triiodide. Purified trimethylbismuth that is substantially free of oxygen-containing impurities and silicon-containing impurities is expected to be obtained.

EXAMPLE 10

The procedure of Example 3 is repeated except that the triethylaluminum is replaced with 290 g of triethylantimony, 15 g of tri-n-propylaluminum are used and the indium trichloride is replaced with 5 g of aluminum trichloride. Purified triethylantimony that is substantially free of oxygen-containing impurities and silicon-containing impurities is expected to be obtained.

EXAMPLE 11

The procedure of Example 2 is repeated except that the triethylaluminum is replaced with 200 g of di-isopropyltellurium, 10 g of trimethylaluminum are used and the aluminum trichloride is replaced with 3 g of tris(dimethylamino) aluminum. Purified di-isopropyltellurium that is substantially free of oxygen-containing impurities and silicon-containing impurities is expected to be obtained.

EXAMPLE 12

The procedure of Example 2 is repeated except that the triethylaluminum is replaced with trimethylaluminum.

EXAMPLE 13

The procedure of Example 1 is repeated except that the following organometallic compounds, catalyst compounds and alkyl-metal compounds are used.

| Example | Organo-metallic Compound | Catalyst Compound (% wt) | Alkyl-metal compound (% wt) |
|---|---|---|---|
| 13A | BPE | AlBr$_3$ (<1) | TIBAl (<2) |
| 13B | DIPMeIn | In(NMe$_2$)$_3$ (<2) | TMIn (<3) |
| 13C | TDMAAs | AlCl$_3$ (<1) | TEAl (<2) |
| 13D | TDMASb | 3:1 AlBr$_3$:KCl (<2) | TNPAl (<3) |
| 13E | TBA | AsCl$_3$ (<1) | TMAl (<2) |
| 13F | TMIn | 9:1 AlCl$_3$:tert-BuLi (<2) | TMAl (<4) |
| 13G | TDMAGe | 8.5:1.5 AlCl$_3$:GeCl$_4$ (<3) | TEAl (<5) |
| 13H | IBGe | 8.5:1.5 GeCl$_4$:KF (<1) | TIBAl (<2) |
| 13I | TMGe | 8.5:1.5 GeCl$_4$:KF (<2) | TMAl (<3) |
| 13J | TDMASi | AlBr$_3$ (<1) | TNPAl (<2) |
| 13K | DMAPDMAl | 7:3 AlCl$_4$:nBuLi (<2) | TMAl (<2) |
| 13L | DIPSe | 8:2 AlBr$_3$:NaCl (<1) | TMAl (<2) |
| 13M | TEMAHf | 8.5:1.5 AlCl$_3$:LiN(EtMe) (<1) | TMAl (<2) |

In the above table, the following abbreviations are used for compounds and ligands: BPE=bisphosphinoethane, DIPMeIn=di-isopropyl methyl indium, TDMAAs=tris(dimethylamino)arsenic, TDMASb=tris(dimethylamino)antimony, TBA=tertiarybutylarsine, TMAl=trimethylaluminum, TEAl=triethylaluminum, TIPAl=tri-isopropylaluminum, TNPAl=tri-n-propylaluminum, TMIn=trimethylindium, TDMAGe=tetrakis(dimethylamino)germanium, IBGe=isobutylgermane, TMGe=tetramethylgermanium, TDMASi=tetrakis(dimethylamino)silicon, DMAPDMAl=dimethylaminopropyl dimethylaluminum, DIPSe=di-isopropylselenide, TEMAHf=tetrakis(ethylmethylamino)hafnium.

What is claimed is:

1. A method of purifying an organometallic compound comprising i) providing a mixture comprising a) an organometallic compound chosen from unsymmetrical dimethyl hydrazine and a compound of the formula $R^1R^2_{n-1}M^1$ wherein $R^1$ is chosen from $(C_1-C_{20})$alkyl, $(C_2-C_{12})$dialkylamino, $(C_1-C_{12})$alkylamino$(C_1-C_{12})$alkyl, di$(C_1-C_{20})$alkylamino$(C_1-C_{12})$alkyl, $(C_2-C_{20})$alkenyl, $(C_2-C_{20})$alkynyl and aryl; each $R^2$ is independently chosen from hydrogen, $(C_1-C_{20})$alkyl, $(C_2-C_{12})$dialkylamino, $(C_1-C_{12})$alkylamino$(C_1-C_{12})$alkyl, di$(C_1-C_{20})$alkylamino$(C_1-C_{12})$alkyl, $(C_2-C_{20})$alkenyl, $(C_2-C_{20})$alkynyl, aryl and halogen; $M^1$ is a Group IIA to Group VIA metal; and n is the valence of $M^1$; and b) a purifying composition comprising an alkyl-metal compound of the formula $R^3_xR^4_{3-x}M^2$ wherein $R^3$ is a $(C_1-C_{20})$ alkyl; each $R^4$ is independent chosen from hydrogen and halogen; $M^2$ is a Group IIIA metal; and x is an integer from 1-3; and a catalyst compound; and ii) heating the mixture.

2. The method of claim 1 wherein the catalyst compound comprises a Group IA, IIA, IIIA or VA metal.

3. The method of claim 2 wherein the catalyst compound further comprises a group chosen from hydrogen, halogen, alkyl, alkenyl, alkynyl, aryl, amino, dialkylamino, aminoalkyl, and dialkylaminoalkyl.

4. The method of claim 1 wherein the catalyst compound is chosen from lithium dimethylamide, tert-butyl lithium, n-butyl lithium, aluminum trichloride, aluminum tribromide, aluminum triiodide, gallium trichloride, indium trichloride, calcium dichloride, barium difluoride, tetramethyl ammonium fluoride, and tris(dimethylamino) aluminum.

5. The method of claim 1 wherein the purifying composition is present in an amount of 0.1 to 10 % wt based on the weight of the organometallic compound.

6. The method of claim 1 wherein the alkyl-metal compound and catalyst compound are present in a weight ratio of 10:1 to 1:10.

7. The method of claim 1 wherein $M^2$ is aluminum.

8. The method of claim 1 wherein $M^1$ is chosen from a Group IIIA metal, a Group IVA metal and a Group VA metal.

9. The method of claim 1 wherein the alkyl-metal compound is a Group IIIA trialkyl compound.

10. The method of claim 1 further comprising a step of removing the organometallic compound form the purifying composition.

* * * * *